(12) United States Patent  
Bracher (10) Patent No.: US 6,237,743 B1  
(45) Date of Patent: May 29, 2001

(54) TABLET TESTER

(75) Inventor: Martin Bracher, Solothurn (CH)

(73) Assignee: Dr. Schleuniger Pharmatron AG (CH)

( * ) Notice: Subject to any disclaimer, the term of this patent is extended or adjusted under 35 U.S.C. 154(b) by 0 days.

(21) Appl. No.: 09/307,958

(22) Filed: May 10, 1999

Related U.S. Application Data (63) Continuation of application No. PCT/EP97/06200, filed on Nov. 7, 1997.
(60) Provisional application No. 60/029,889, filed on Nov. 8, 1996.

(51) Int. Cl.$^7$ .................................................. B65G 43/08
(52) U.S. Cl. ................. 198/464.2; 209/680; 198/468.11
(58) Field of Search ............................. 198/741, 468.1, 198/443, 444, 360, 464.2, 718; 209/615, 680

(56) References Cited

U.S. PATENT DOCUMENTS

| | | | |
|---|---|---|---|
| 1,857,808 | * | 5/1932 | Diederichs . |
| 4,219,986 | * | 9/1980 | Osterhaus ................................ 53/314 |
| 4,434,887 | * | 3/1984 | Yager ..................................... 198/391 |
| 4,542,646 | * | 9/1985 | Smith et al. ............................... 73/78 |
| 4,660,713 | * | 4/1987 | Kaminski ............................. 198/443 |
| 4,784,275 | | 11/1988 | Fridge . |
| 5,190,162 | * | 3/1993 | Hartlepp ............................... 209/583 |
| 5,240,118 | | 8/1993 | Mayer . |
| 5,522,512 | | 6/1996 | Archer et al. . |

FOREIGN PATENT DOCUMENTS

| | | | |
|---|---|---|---|
| 37 11 827 A1 | 10/1988 | (DE) | ............................. B65G/47/14 |
| 89 11 221 U | 12/1989 | (DE) | ............................. B65G/47/71 |
| WO 85/03278 | 8/1985 | (WO) | ............................ B65G/47/14 |

OTHER PUBLICATIONS

PCT/EP97/06200 International Preliminary Report Translation dated May 11, 1999 (7 pages).

* cited by examiner

Primary Examiner—James R. Bidwell (57) ABSTRACT

A tablet tester has a screw-like vibratory conveyor and isolating unit, a positioning unit having a transport rake and an orientation unit between the two first-mentioned units, which in particular is in the form of a linear vibratory conveyor. A sensor arrangement triggers the transport rake and permits automatic ejection of tablet residues via a fragment trap.

26 Claims, 11 Drawing Sheets

TABLET TESTER

This is a continuation of Internation Application PCT/EP97/06200 filed Nov. 7, 1997, of the same inventor, and claims benefit of Provisional application Ser. No. 029,889 filed Nov. 8, 1996.

BACKGROUND OF THE INVENTION

1. Field of the Invention

This is a continuation of International Application PCT/EP97/06200 filed Nov. 7, 1997, of the same inventor.

The invention relates to a tablet tester.

Tablet testers are apparatuses which are used mainly in the pharmaceutical industry or in science and research. Since medicaments which are administered in tablet form must in some cases meet very precise quality and quantity requirements, parameters of the respective tablets which are determined at least on random samples are measured.

2. Discussion of Relevant Art

Apparatuses which accommodate a plurality of testing or measuring stations and in which tablets are transported from a storage container to the individual station are known for such measuring processes. An example of such an apparatus is the combination tablet tester "Multicheck" from ERWEKA, D-63150 Heusenstamm. It permits the automatic or computer-controlled measurement of weight, thickness, diameter and hardness of individual tablets, which have to be delivered in succession from a storage container.

However, it is precisely the individual delivery of tablets that is a problem in such apparatuses. Thus, the very company mentioned is attempting, by means of EP-B1-170670, to describe a particularly suitable transport means for tablets within such a combination tablet tester. The transport means is designed in such a way that a rake having V-shaped forks pushes the tablets over a guide track which has exactly dimensioned holes through which unsuitable tablets are intended to fall. This apparatus thus forms a sort of sieve, the size of the tablets and their (accidental) position relative to the forks determining whether they are transported further or fall through the holes. There remains therefore an uncertainty which may lead to delays in measurement or incorrect measurements. Apart from this, the solution offered by ERWEKA may be susceptible to faults in the region in which the tablets are fed to the rake or cannot always ensure that the tablets also reach the required position and enter the rake individually. For some of the individual measuring stations, it is in fact important whether the tablets are vertical or horizontal and whether they are delivered longitudinally or crosswise. If more than one tablet is present in a fork of the rake, these tablets cannot be measured or the result is a rejected measurement.

On the other hand, the rejection of tablet fragments before passage through the measuring stations is not ensured in the known apparatus, so that here too incorrect measurements can occur.

There is thus no satisfactory, universal technique in this context particularly for different tablet shapes. This leads to the necessity of conversions for different tablet shapes or to a loss of time during measurement.

In an attempt to improve the situation, Norbert Krämer of D-6100 Darmstadt has provided a relatively complicated isolating apparatus having baffles for tablets, which is described in DE-C2-3711827. His apparatus is intended to isolate tablets over particularly short distances. However, this description offers no solution for further transport to the individual measuring stations. Furthermore, the problem of positioning and of the rejection of tablet fragments is not solved by Krämer.

Another manufacturer, Elisabeth Hata, uses Krämer's isolating apparatus but without its baffles, which leads to adequate isolation in the case of relatively large tablets but to trouble-prone isolation in the case of smaller tablets.

SUMMARY OF THE INVENTION

It is therefore the object of the invention to provide a tablet tester which effects fault-free isolation, places the tablets in the correct position and as far as possible is universally applicable for a very wide range of tablet shapes. Incorrect measurements are to be avoided during operation, thus permitting in general faster measurement than in the past.

This object is achieved by the combination of individual apparatuses known per se in an inventive manner. Some of these apparatuses have furthermore been improved in an inventive manner compared with the known apparatuses.

The general structure consists, according to the invention, of an isolating unit, which is preferably in the form of a conventional "EMSE" vibratory screw conveyor having a chute, an orientation unit which is in the form of a linear vibratory conveyor converted according to the invention. A particular further development provides a tablet sensor having an inventive fragment trap and a special positioning rake above a transport surface, which transports the previously correctly positioned tablets, checked for waste, to measuring stations, as far as a residue trap.

This object is achieved according to the invention by a tablet tester comprising at least one measuring station and a conveyor that conveys and isolates tablets, having a downstream orientation unit and a positioning rake connected thereto above a transport surface that transports said tablets to said measuring station, wherein said orientation unit comprises a linear vibratory conveyor that has a structure L-shaped in cross-section and an inclination portion and a radius between two limbs of the L-shape, which conveyor has a horizontal conveying surface in a region where said conveyor enters said positioning rake. The specification describes inventive embodiments which can also be used independently and regardless of the main concept of the solution.

BRIEF DESCRIPTION OF THE DRAWINGS

Further details, advantages and potential applications of these solutions are presented in the description of the Figures.

The information in this context in this patent application should be understood as being merely by way of example in that detailed solutions other than those described are also possible within the scope of the patent claims.

FIG. 6 shows the residue trap at the end of the rake and FIG. 7 shows an exemplary detailed drawing of a tablet sensor in plan view, FIG. 7a showing the closed sensor and FIG. 7b showing the opened sensor with exposed fragment trap.

DETAILED DESCRIPTION OF PREFERRED EMBODIMENTS

The Figures are described in relation to one another, identical parts being denoted by the same reference symbols.

Figure 1:
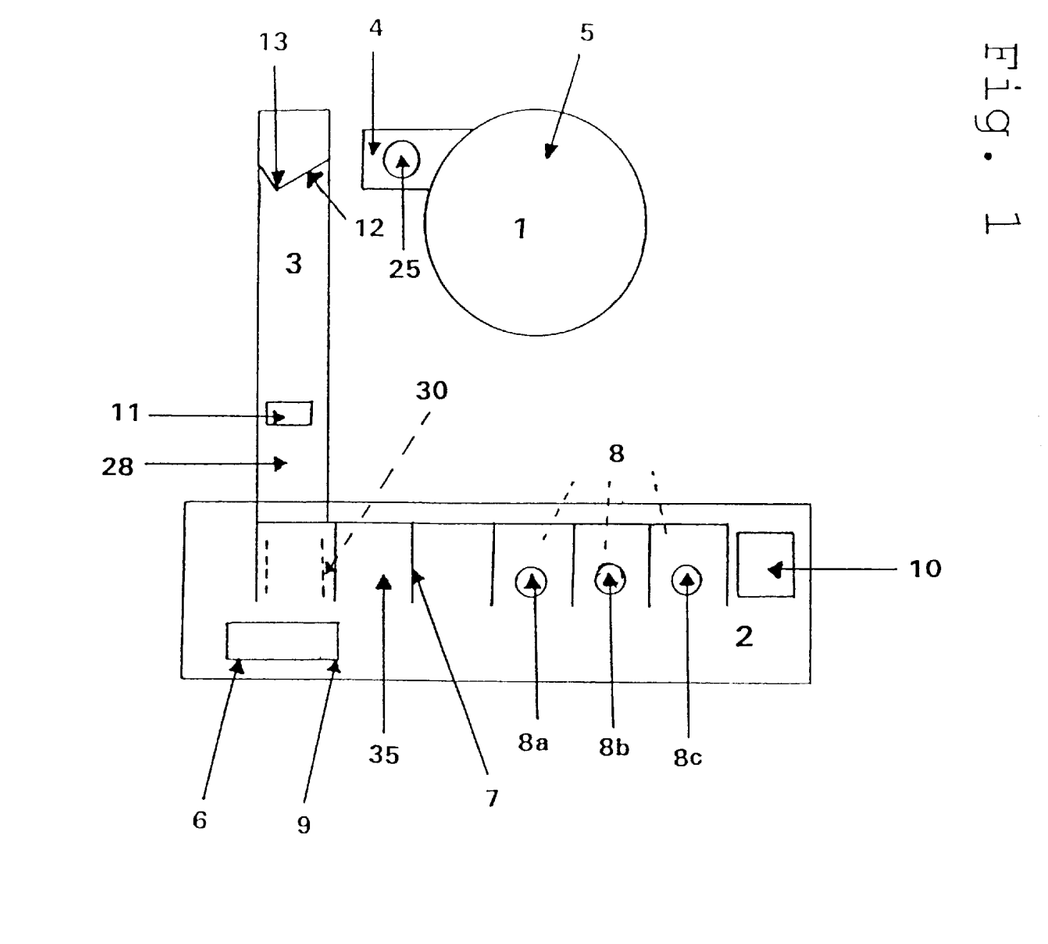
FIG. 1 shows a symbolic setup in plan view.

FIG. 1 shows a conventional vibratory screw conveyor 1 having a feed hopper 5 whose outlet ends in a chute 4. The vibratory conveyor isolates tablets and transports them against the force of gravity into the chute 4. Connected to this is a specially designed orientation unit 3 which could also be used independently in other comparable apparatuses.

The special feature of this unit which may also be used independently and which essentially consists of a linear vibratory conveyor is an inclination 12 which is shown in section and which results in the tablets—provided that they have an elongated structure—being oriented in the longitudinal direction parallel to the orientation unit 3. Toward the end of the orientation unit 3, the inclination 12 connects, according to the invention, with an approximately horizontal conveying surface 28. At the lowest point of the orientation unit 3, the latter is provided with a radius 13 which causes upright tablets to fall over so that they rest with their broad side on the inclination 12 and then on the conveying surface 28.

Figure 9:
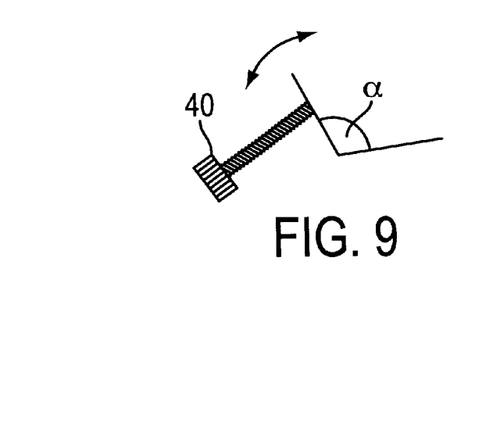
FIG. 9 shows an adjustment arrangement for the radius of a linear vibratory conveyor.

As shown in FIG. 9, the angle a of the radius 13 is adjustable by a spring-based adjusting screw 40.

Figure 10:
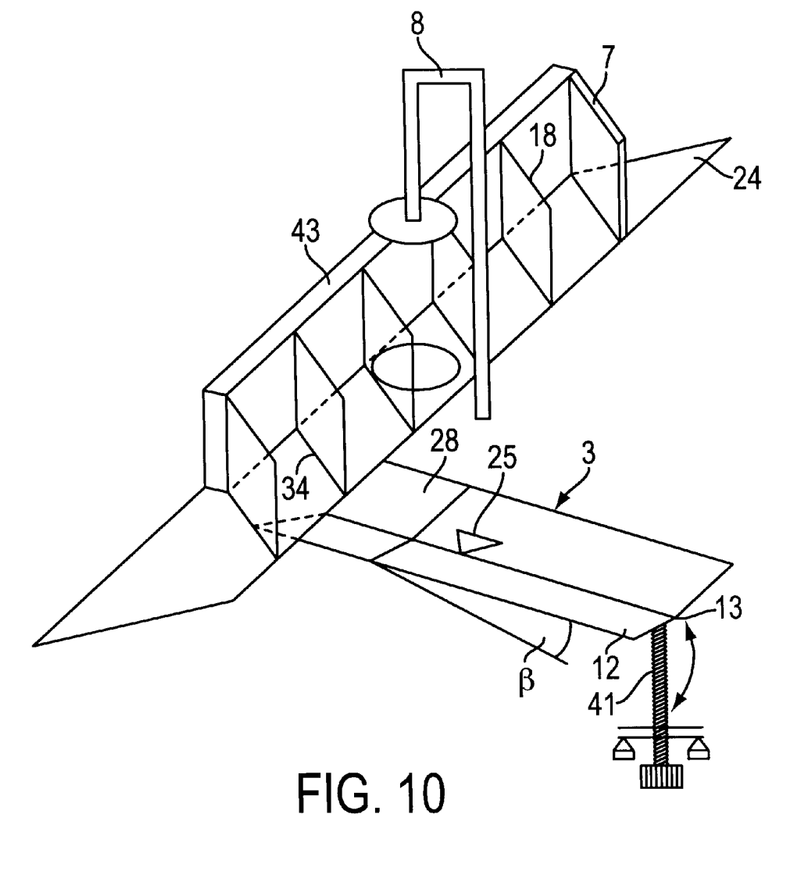
FIG. 10 shows an adjustment arrangement for inclination of the linear vibratory conveyor.

FIG. 10 shows an arrangement 41 for adjustment of the inclination angle β of the orientation unit 3. FIG. 10 also shows prongs 18 of the positioning rake 7 that are pivotable on the wall 43 of the rake 7 to receive tablets conveyed to the transport surface 24 by the orientation unit 3.

For particularly difficult tablet shapes, it is also possible to arrange baffles 11 which can force a tablet 25 on the one hand to fall over but on the other hand also to adopt a certain longitudinal or crosswise orientation. According to the invention, these baffles 11 can easily be removed or replaced so that they can be changed if required, without having to interrupt operation for a long time. Owing to the carefully thought out shape of the orientation unit 3 with inclination 12 and radius 13, however, the use of baffles 11 can be dispensed with for most tablet shapes.

The orientation unit 3 connects with a positioning unit 2, at the beginning of which a fragment trap 9 is mounted and at the end of which a residue trap 10 is mounted. The positioning unit 2 holds measuring stations 8 and has a laterally displaceable positioning rake 7 with prongs 18 for laterally conveying tablets 25 to the individual measuring stations 8, for example a weighing cell 8a, a thickness measuring station 8b and a hardness measuring station 8c.

Figure 11:
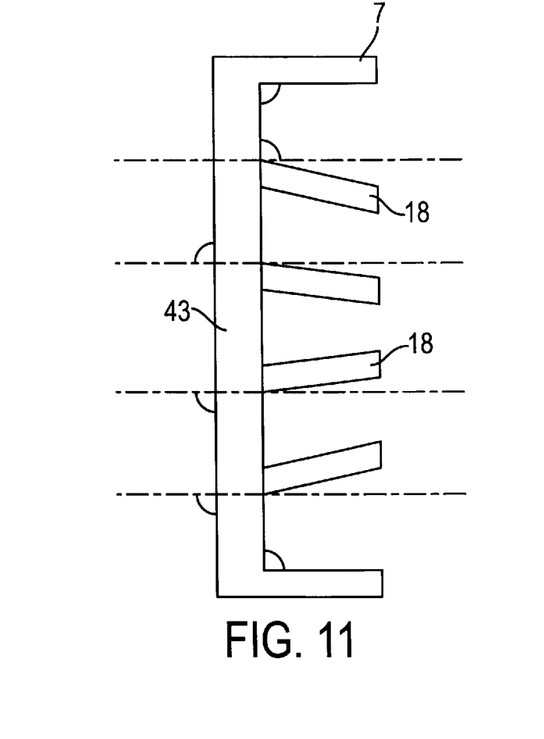
FIGS. 11 and 12 show adjustable or pivotable prongs of a rake.
Figure 12:
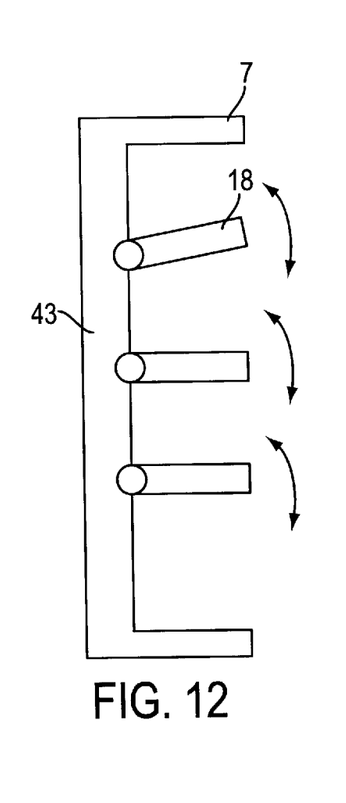

As shown in FIGS. 11 and 12, according to the invention, some of the prongs 18 are inclined slightly more than 90° from the feed direction (cf. angle 30). This leads to an automatic displacement vector at the conveyed tablets 25 in the direction of the front support wall 31, which is advantageous in that individual measuring stations 8 with their structures are also oriented relative to the support wall 31 and it is important that the tablets 25 arrive at these structures in the correct position. For the purposes of the invention, it is of course also possible to provide a different inclination of the prongs 18, for example in the other direction, if the tablets 25 are also to be moved away from the support wall 31 during their further transport. This possibility also includes adjustable inclinations of the prongs 18 in order to be able to adapt them to changing circumstances.

Figure 13:
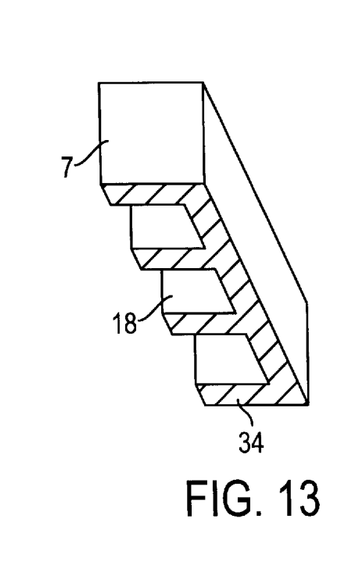
FIG. 13 shows brushes or felt strips on the underside of prongs of a rake.

According to a particular embodiment (FIG. 13), the prongs 18 have, on their lower side, brushes 34, a felt strip or the like, which serve to free the guide track from dust (tablet dust). By moving the rake 7, this is optimally effected simultaneously with the conveying of the tablets. The rake 7 executes a lateral displacement, is then raised and is moved back through the same lateral displacement distance and then lowered again, and the next lateral displacement can be carried out.

The last measuring station 8c has, as a special feature according to the invention, an elongated indentation 32 which permits final longitudinal positioning of elongated tablets before they are gripped by the clamping jaws 33a, b.

According to a particular embodiment of the invention, clamping jaws 33 and the final prong 18 are designed in such a way that caked tablet residues on the jaws 33 and/or on the guide plane are eliminated. The results of the measurement are thus optimized.

Figure 7A:
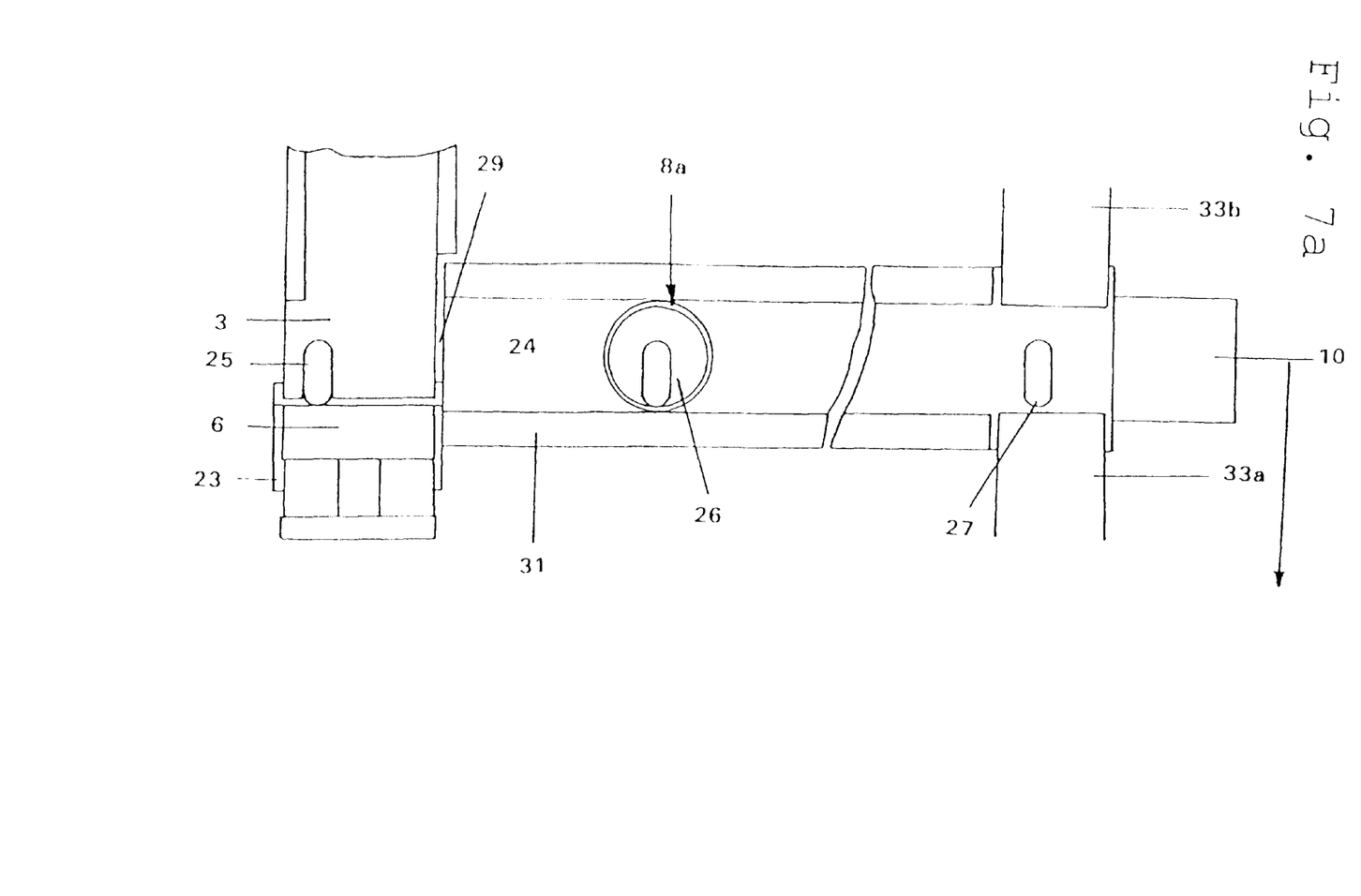

According to the invention, the first fragment trap 9 is covered by a tablet sensor 6 which, on arrival of a tablet 25, triggers the transport rake 7 and at the same time opens a gap of, for example, 3 mm (cf. FIG. 7a) in order simultaneously to allow tablet fragments also delivered to drop downward.

In the case of an impermissible double delivery, the sensor 6 according to the invention can also detect this and can open the fragment trap 9 in order to prevent further errors.

For the purposes of the invention, "sensor" also includes a straightforward, releasable "stop" for tablet residues or the like, provided that this is controlled as a function of the conveyed tablets or tablet residues. In particular, the sensor may also comprise a light barrier, optionally with an image-forming optical system. In one embodiment, however, the sensor is designed as a mobile slide provided with a piezo-electric switching surface.

Figure 7B:
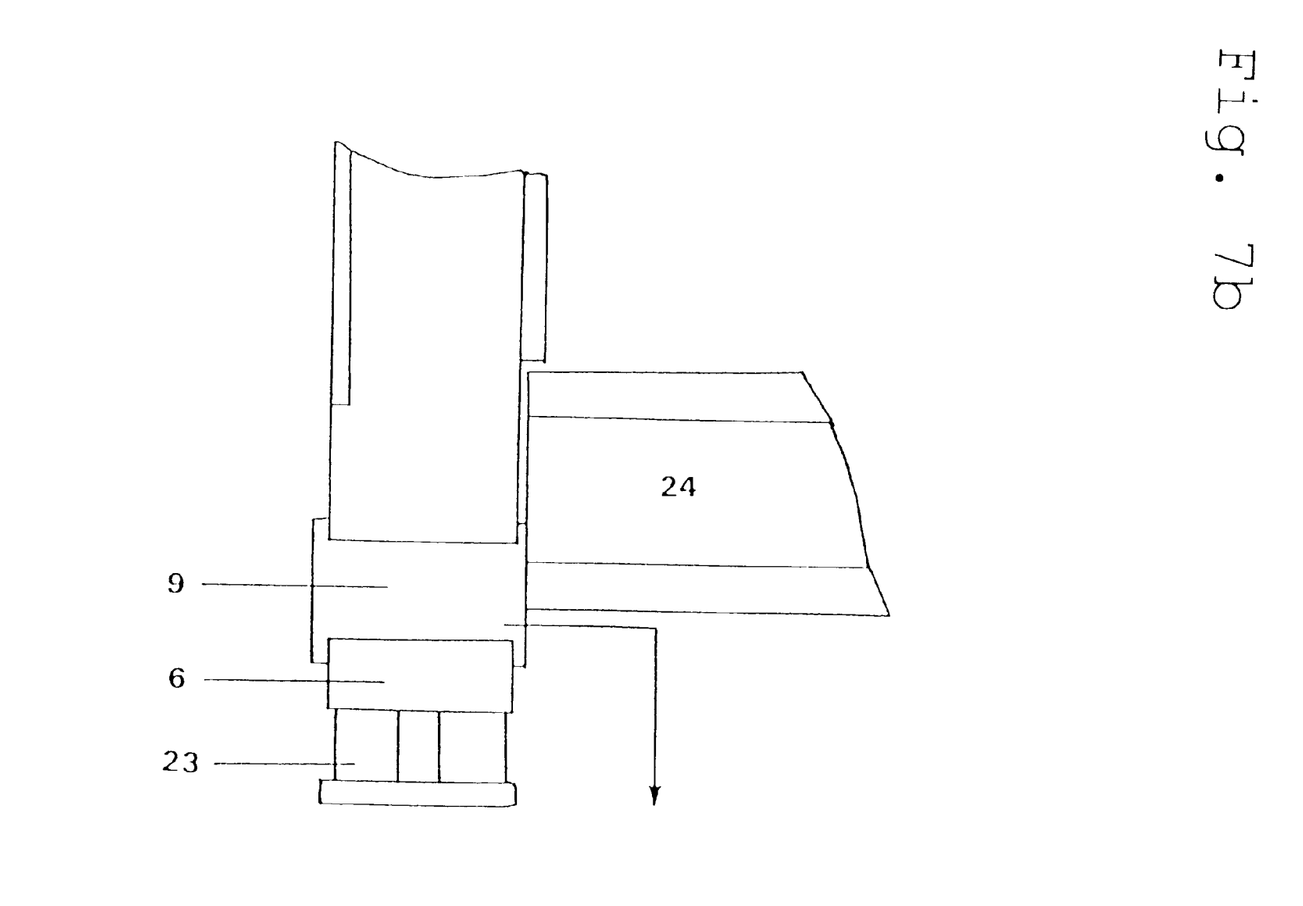
Figure 8A:
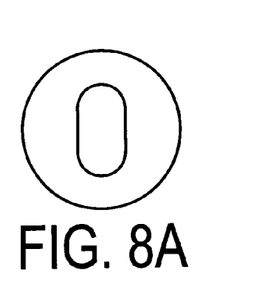
FIGS. 8a–8f show interchangeable support disks to support tablets of different shapes and sizes at a hardness measuring station.
Figure 8B:
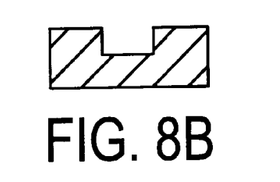
Figure 8C:
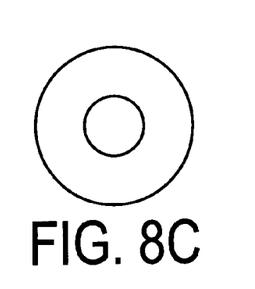
Figure 8D:
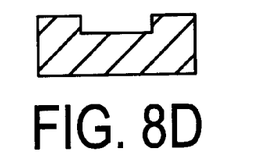
Figure 8E:
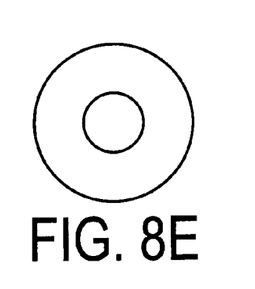
Figure 8F:
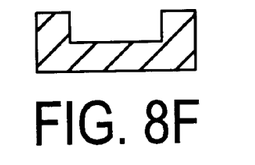

In a particular variant of the sensor 6, the latter has, for example, optical measuring sensors which are known per se, are not shown, detect the completeness of a tablet 25 and, in the negative case, open the gap to such an extent that even large fragments can fall downward through the fragment trap 9 (cf. FIG. 7b).

A possible sensor setting would be, for example, as follows: if a tablet having a diameter of 6 mm arrives, said sensor travels back briefly to the gap width of 2–3 mm and then forward again so that the tablet comes to rest 1–2 mm before the support surface of the support wall 31. By widening the gap, any fragments fall away; by pushing back the tablet 25, the latter is positioned for certain measuring stations.

Also within the scope of the invention are of course variants having a particular software control which makes it possible, for example, to transport excess tablets from a measuring series out of the vibratory screw conveyor 1 and the orientation unit 3 by virtue of the fact that, after a certain tablet quantity detected by the sensor and further conveyed by means of rake 7, the fragment trap 9 is opened by the sensor.

The traps 9 and 10 each enter a box 15 at the front of the apparatus, so that these can be emptied in a user-friendly manner, which is also a particular advantage of this variant of the invention.

A transparent cover 14 protects the apparatus from dust and undesired access without obscuring the functions or the correct functional sequence.

Figure 2:
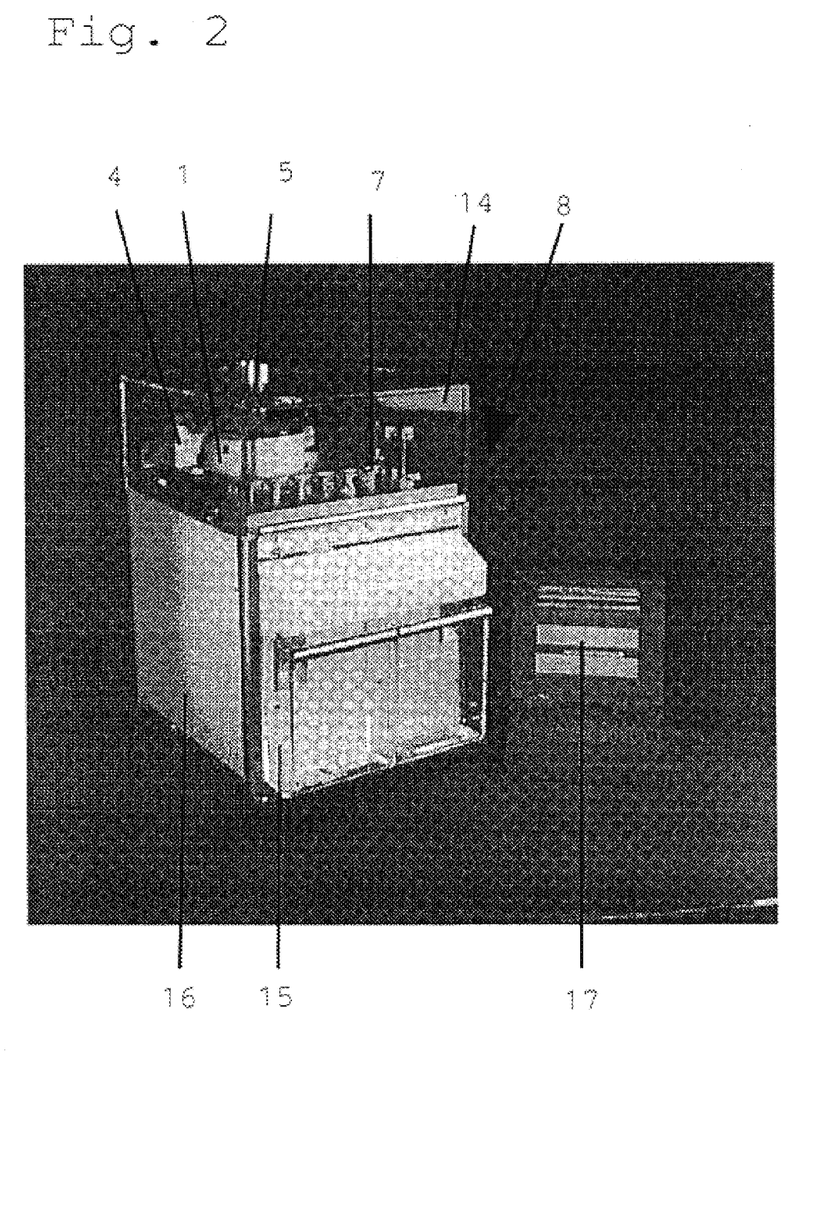
FIG. 2 shows a prototype setup in oblique view.
Figure 3:
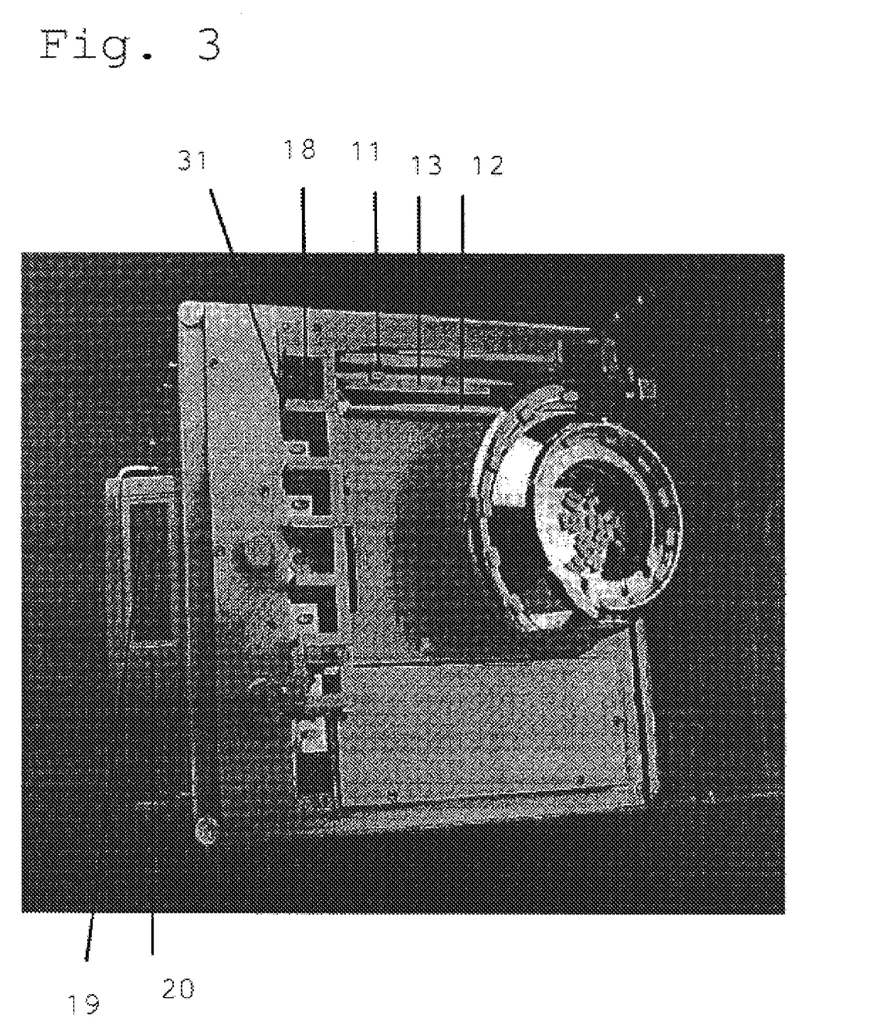
FIG. 3 shows the prototype setup in plan view without a cover.
Figure 4:
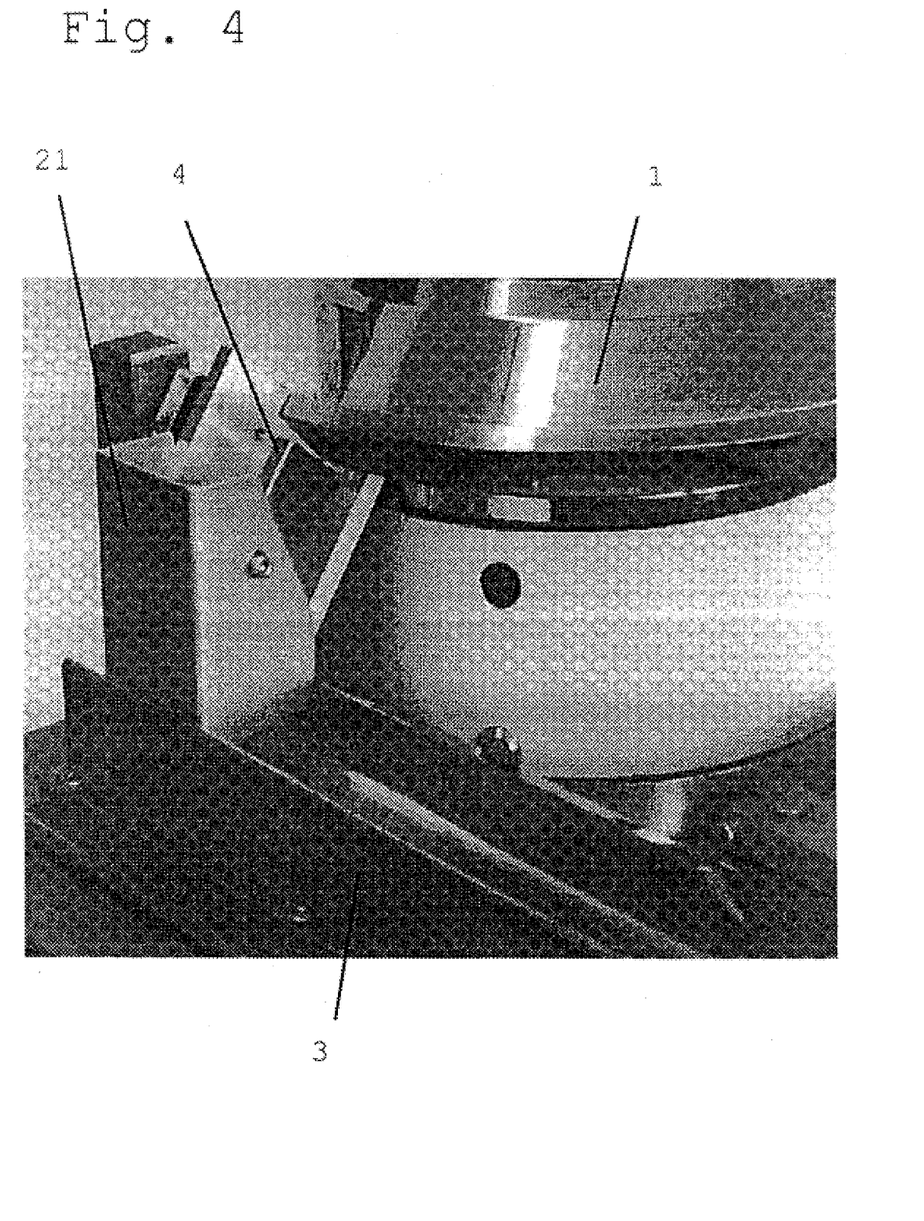
FIG. 4 shows the transfer from a screw conveyor to a linear conveyor in the prototype setup.
Figure 5:
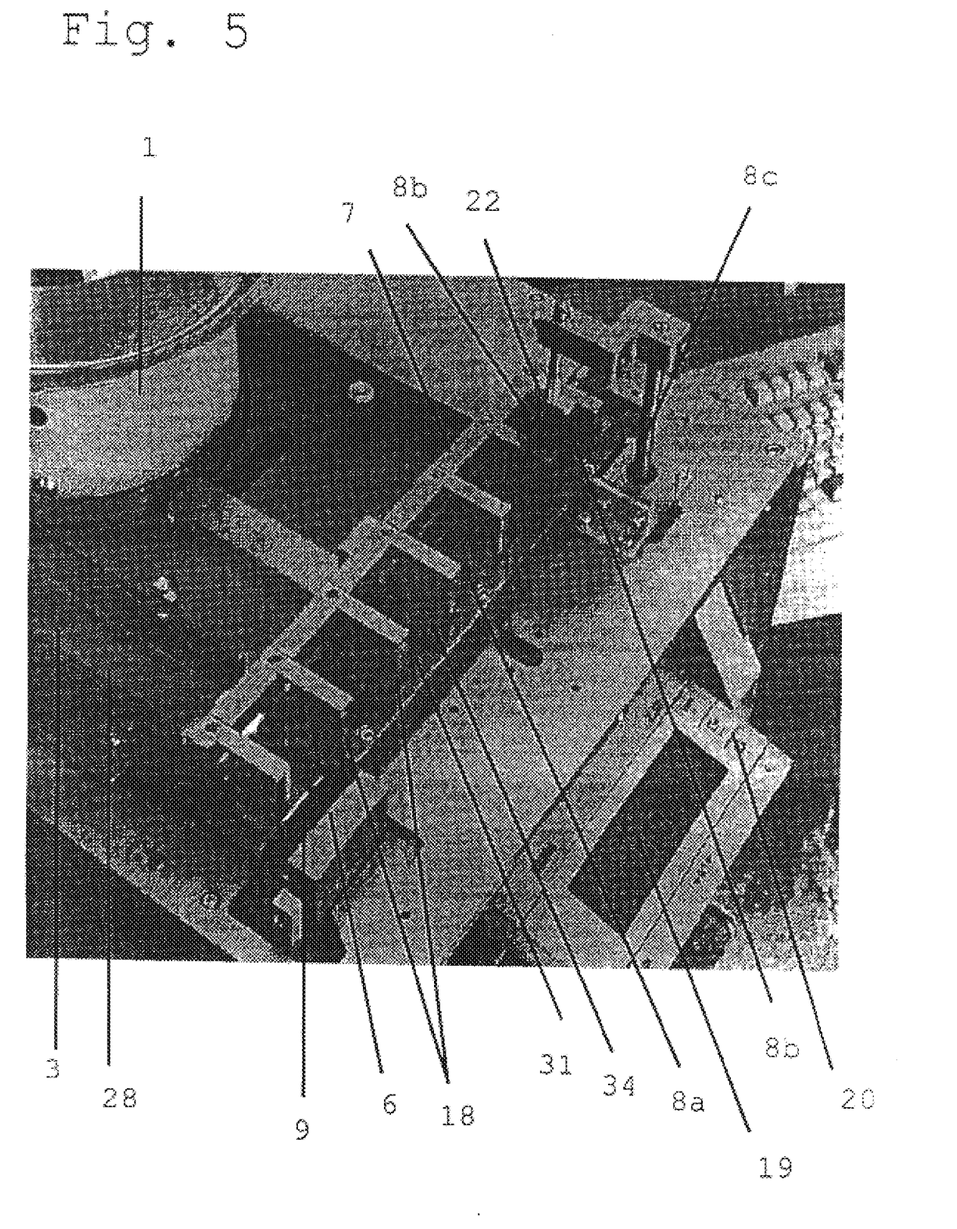
FIG. 5 shows a rake in the prototype.
Figure 6:
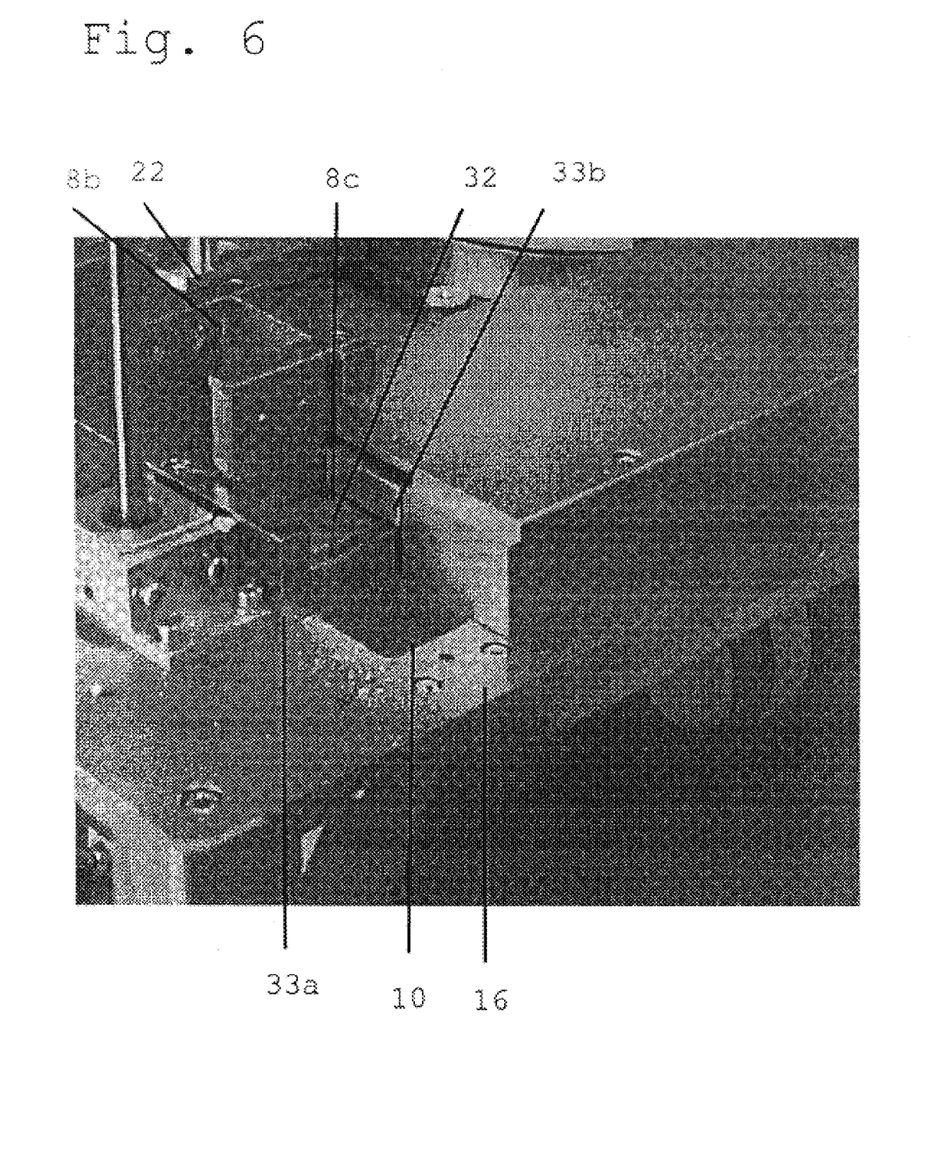

An optionally coverable (FIG. 2) display 19 and an input unit 20 (FIG. 5) permit the control of the apparatus, unless it is in any case controlled by means of computer 17 (FIG. 2).

The drives and electrical controls of the apparatus are housed in the interior of a rack 16 which carries the parts described.

In a particular embodiment of the invention, all running surfaces or sliding surfaces with which the tablets 25 may come into contact are provided with a low-friction treatment, for example electrolytically polished, provided with high-gloss chromium plating or polished.

In a further embodiment of the invention, the weighing pan 26 of the weighing cell 8a is arranged in such a way that its axis transverse to the transport direction is identical to the transverse axis of a conveyed tablet, whereas the central axis of a tablet parallel to the support wall 31 does not necessarily correspond to the central axis of the weighing pan 26. Preferably, the tablet is as close as possible to the support wall 31, just so that its full circumference rests on the weighing pan 26. This can also be achieved, inter alia, if the sensor 6 comes to rest with its stop edge about 1.5 mm before the support surface of the support wall 31—and if necessary is moved forward.

Further information regarding the Figures is shown in the list of reference symbols.

The invention is not restricted by the embodiments stated so far. It covers a broader range:

For the purposes of the invention, "tablets" also mean "capsules" or the like.

"Baffles" also include "deflectors" and can, if required, also be formed by air nozzles or the like.

Air or vacuum nozzles can moreover be mounted in a plurality of locations, in a manner not described in detail, for example for the purpose of automatic cleaning, just as compressed air may also be provided for controlling the mechanical components.

In a further variant, the orientation unit 3 can also be provided with a diverter or a sensor ejector which, independently of the sensor 6, can influence control of tablets. For example, isolation which is not yet satisfactory can thus be monitored and corrected. On the other hand, it would also be possible for a plurality of tablets to be present directly one behind the other in the orientation unit and to be further transported singly by opening such a diverter. As a rule, however, the tablets should be delivered singly.

As a further variant, it is possible to design the chute 4 to be rotatable, so that a further facility for emptying into a further container not shown is possible. However, owing to the sensor properties according to the invention, this will generally be superfluous.

In a further particular embodiment of the invention, the positioning or transport rake is provided with laterally adjustable or pivotable prongs 18 which are adjusted as a function of the width of tablets so that tablets whose longitudinal dimension is at right angles to the transport direction are moved in exactly this position. The prongs 18 of the transport rake thus rest laterally against tablets as soon as the latter are moved in the transport direction. After the movement of the tablets, the prongs open slightly, are then raised as in the variant described above and are moved back in order to grip the next tablets and to transport them. This prong movement is automatically controlled as a function of the tablet structure. This particular embodiment has the advantage that even tablets arriving in a slightly skew position can be correctly positioned and that moreover, with transport by means of the transport rake, the tablets cannot be accidentally swivelled out of their position. The opening of the prongs shortly before raising of the transport rake is advantageous according to the invention because it avoids the tablets being accidentally set on edge as a result of friction against the prong walls.

A further particular embodiment is provided in the region of the hardness measuring station 8c. Instead of the indentation 32 as shown in FIGS. 8a–8f, it is also possible to provide there an interchangeable support disk which has a comparable indentation, the different support disks having different indentations. Tablets are in fact produced in different sizes, so that the function of the apparatus is improved if the indentation 32 is adapted to the tablet size. An indentation 32 which is too narrow would not produce a positioning effect since the excessively broad tablet would not sink into the indentation. A smaller tablet on the other hand could sink too deep in the indentation 32 so that the press jaws cannot engage the tablet optimally.

LIST OF REFERENCE SYMBOLS

1. Isolating unit or vibratory screw conveyor
2. Positioning unit
3. Orientation unit with linear vibratory conveyor
4. Chute
5. Feed hopper
6. Tablet sensor
7. Positioning rake or transport rake
8. Measuring stations
8a. Weighing cell
8b. Thickness measuring station
8c. Hardness measuring station
9. Fragment trap
10. Residue trap
11. Baffles
12. Inclination; can if necessary also be adjustable
13. Radius; can if necessary be adjustable or interchangeable
14. Cover
15. Box
16. Rack
17. Computer
18. Prongs
19. Coverable display
20. Input field/input unit
21. Chute cover
22. Measuring slide
23. Drive/brush
24. Conveying track
25. Tablet
26. Weighing pan
27. Positioning recess
28. Approximately horizontal conveying surface 29. Gap
30. Angle
31. Support wall
32. Indentation, positioning recess
33. Clamping jaws
34. Brushes
35. Conveying surface

I claim:

1. A tablet tester comprising:
at least one measuring station, and an orientation unit and a positioning rake associated therewith above a transport surface, which positioning rake transports said tablets to said measuring station, by shifting towards said measuring station in a lowered position and shifting back in a raised position to allow a tablet to enter said rake, wherein said orientation unit comprises a linear vibratory conveyor that has a structure L-shaped in cross-section with an inclination portion and a radius between two limbs of said L-shaped structure, which linear vibratory conveyor has a horizontal conveying surface in a region where said linear vibratory conveyor enters said positioning rake.

2. The tablet tester as claimed in claim 1, further comprising a tablet sensor arranged at an entrance of said positioning rake, which detects incoming tablets and triggers said positioning rake.

3. The tablet tester as claimed in claim 2, further comprising a fragment trap, wherein said tablet sensor comprises a slide that can be driven by a motor and which makes said fragment trap openable and closable to receive incomplete tablets.

4. The tablet tester as claimed in claim 3, wherein said tablet sensor has a light barrier or a piezoelectric surface switch, which makes incoming tablets detectable.

5. A tablet tester according to claim 3, wherein the opening or closing of the fragment trap is program controlled.

6. A tablet tester according to claim 3, wherein the opening or closing of the fragment trap is sensor controlled.

7. The tablet tester as claimed in claim 1, wherein said linear vibratory conveyor has interchangeable baffles to properly orient said tablets on said inclination portion.

8. The tablet tester as claimed in claim 1 further comprising a vibratory screw conveyor.

9. The tablet tester as claimed in claim 8, further comprising a chute arranged between said vibratory screw conveyor and said linear vibratory conveyor, said chute providing a dust separation gap.

10. The tablet tester as claimed in claim 9, wherein said chute is moveable by a motor in order to permit emptying of said vibratory screw conveyor.

11. The tablet tester as claimed in claim 1, wherein said transport surface is L-shaped in section and has a perpendicular limb forming a support wall along which said measuring stations are arranged integrated in said transport surface, and wherein said conveyor further comprises a residue trap at an end of said transport surface.

12. The tablet tester as claimed in claim 1, wherein said positioning rake has prongs which, viewed from above, are inclined relative to its transport direction by an angle which is not equal to 90°.

13. The tablet tester according to claim 12, wherein said prongs are formed in such a way that they clean parts of said measuring stations during a conveying movement or a resetting movement of said prongs.

14. The tablet tester as claimed in claim 1, wherein said positioning rake has prongs that are adjustable or pivotable.

15. The tablet tester as claimed in claim 14, wherein said prongs are adjustable or pivotable automatically as a function of tablet dimensions.

16. The tablet tester as claimed in claim 1, wherein said measuring station comprises a hardness measuring station and interchangeable support disks provided in the region of said hardness measuring station.

17. The tablet tester as claimed in claim 16, wherein said interchangeable support disks are interchangeable as a function of tablet dimension.

18. The tablet tester as claimed in claim 1, further comprising a fragment trap and a residue trap, a rack carrying said orientation unit, said positioning rake and boxes arranged on the front side rack that are assigned to said fragment trap and said residue trap.

19. The tablet tester as claimed in claim 1, wherein all surfaces which come into contact with said tablets are surface-treated, polished or the like.

20. The tablet tester as claimed in claim 1, wherein said inclination portion of said linear vibratory conveyor is adjustable.

21. The tablet tester according to claim 1, wherein said radius is adjustable.

22. The tablet tester according to claim 1, wherein said prongs have at least one of brushes, felt strips and other sweeping surfaces on their side facing said transport surface.

23. A tablet tester comprising:
a positioning rake, and
a tablet sensor arranged at an entrance of said positioning rake that detects incoming tablets and triggers said positioning rake, and triggers a slide that opens a fragment trap.

24. A tablet tester according to claim 23 wherein said tablet sensor has a light barrier or a piezoelectric surface switch that detects incomplete tablets.

25. A tablet tester according to claim 23 wherein said sensor senses the completeness of a tablet and opens said fragments trap to receive incomplete tablets.

26. A tablet according to claim 23, wherein said sensor comprises an image forming optical measuring sensor.

* * * * *